United States Patent [19]

Mileikowsky

[11] 4,409,990
[45] Oct. 18, 1983

[54] FLUID SAMPLING NEEDLE ASSEMBLY AND METHOD OF USE THEREOF

[76] Inventor: Gil N. Mileikowsky, 2601 S. Braeswood, #902, Houston, Tex. 77025

[21] Appl. No.: 310,521

[22] Filed: Oct. 13, 1981

[51] Int. Cl.³ .............................................. A61B 5/14
[52] U.S. Cl. .................................. 128/763; 128/772; 604/280; 604/272
[58] Field of Search ................ 128/760, 762–765, 128/768, 772, 218 N, 218 D, 218 DA, 218 G, 218 R, 215–216, 221, DIG. 16; 604/51–53, 93, 158, 171, 239, 264, 272, 280

[56] References Cited

U.S. PATENT DOCUMENTS

| 3,200,813 | 8/1965 | Christakis | 128/218 R X |
| 3,584,624 | 6/1971 | de Clutiis | 128/221 X |
| 3,877,465 | 4/1975 | Miyake | 128/764 |
| 3,903,885 | 9/1975 | Fuchs | 128/DIG. 16 X |
| 4,041,934 | 8/1977 | Genese | 128/763 |
| 4,072,146 | 2/1978 | Howes | 128/768 X |
| 4,108,175 | 8/1978 | Orton | 128/768 X |
| 4,140,108 | 2/1979 | Nugent | 128/2 F |
| 4,166,450 | 9/1979 | Abramson | 128/764 |

Primary Examiner—Lee S. Cohen
Assistant Examiner—Angela D. Sykes
Attorney, Agent, or Firm—Kirkland & Ellis

[57] ABSTRACT

A fluid transport assembly, comprising a cannula spaced apart from a needle, with the cannula and needle lying along the same longitudinal axis and separated by a rigid needle housing assembly is provided. The cannula and the first end of the needle housing assembly are adapted for mating engagement with a catheter prepositioned in a blood vessel of a patient. The needle and second end of the needle housing assembly are adapted for engagement with a standardized collection container, with the container preferably supported by a holder which is threadably secured to threads positioned in the second end of the needle housing assembly. The cannula is made of a flexible material and is provided with a non-cutting tip; the needle is made of a rigid material and is provided with a cutting tip. The present invention is adapted for use at an intravenous insertion site, thereby obviating the necessity for a second needle insertion site.

5 Claims, 5 Drawing Figures

FLUID SAMPLING NEEDLE ASSEMBLY AND METHOD OF USE THEREOF

BACKGROUND OF THE INVENTION

1. Field of Invention

The present invention is used to transport fluid and is principally useful in collecting samples of fluid from a single patient.

2. Description of the Prior Art

The difficulties inherent in obtaining anything other than a single sample of blood at one sitting from a particular patient have long been recognized and assemblies for such use have been patented. Nugent, U.S. Pat. No. 4,140,108, teaches the use of a sheathed needle mounted on a threaded hub which can be readily adapted to standard blood collection containers. However, Nugent does not teach the use of a flexible, non-cutting cannula which can be used to conveniently draw blood from a catheter prepositioned in the lumen of a blood vessel. Abramson, U.S. Pat. No. 4,166,450, discloses the importance of ensuring that the extraction needle is properly located in the lumen of the blood vessel before atttaching a blood collection container, but discloses the need to either allow a metal needle assembly to remain in place in the vessel or remove that assembly and reinsert a comparable assembly at another insertion site at a later time.

The present state of the medical art requires multiple needle insertions as fluid samples are needed and is at best uncomfortable for the patient who must tolerate multiple needle insertions.

The present invention is particularly advantageous in that it provides a more comfortable, economic and effective way to extract samples of fluid than the prior art while making maximum use of existing sampling and intervenous insertion technology and significantly decreasing discomfort to the patient. In particular, the present invention provides an apparatus and method useful for obtaining one or more fluid samples from a patient from an insertion site into which has been placed a catheter.

BRIEF DESCRIPTION OF THE INVENTION

The present invention is used in collecting samples of fluid from a single patient without requiring multiple needle insertions. The invention provides a lightweight, one-piece assembly for transfer of fluid from a patient to standardized collection containers.

In particular, the present invention provides a needle assembly which comprises a flexible, non-cutting cannula and a rigid, cutting needle separated by a rigid cannula and needle housing assembly. The needles are mounted in the needle housing assembly along the longitudinal axis thereof so that the first end of th cannula is distal to the second end of the needle and the second end of the cannula is proximal to the first end of the needle. The cannula is advantageously constructed of a flexible material and the first end thereof is provided with a non-cutting tip. The needle is constructed from a rigid light weight metal or synthetic material and has a cutting tip on the second end thereof.

The cannula is adapted for communication with the fluid source by being slidably mated with an intravenous catheter which is prepositioned within the lumen of a blood vessel.

The fluid sample enters through the first end of the cannula and flows through the bore of the cannula to the first end of the needle. Fluid also can pass through the bore of the needle. The second end of the needle is covered by flexible, rubber-like sheath.

The two cannula and needle are aligned along the same longitudinal axis and are held in place by a rigid needle housing assembly. The first end of the needle housing assembly is adapted to mate with an exposed end of the catheter. Preferably, the second end of the needle housing assembly is threaded to permit coupling with the threads of a standard fluid collection container holder. With the container holder threadably secured to the second end of the needle housing assembly, the covered end of an evacuated fluid collection container may be pressed against the second end of the needle. The cutting edge of the needle pierces first a protective sheath surrounding the needle and then the cover of the evacuated fluid collection container, thereby causing the fluid sample to flow from the blood vessel through the cannula, the housing assembly and the needle and to discharge directly into the collection container. When the container is removed, the sheath of the needle returns to its original position and seals off the flow of fluid. This procedure may be repeated until such time as the catheter is used in conjunction with an intravenous fluid supply device, it being appreciated that intravenous fluid introduced into the patient through the catheter will dilute the patient's blood in the region surrounding the insertion site. In addition, the cannula may be advantageously coated (either internally, externally or both) with an anticoagulant, such as Heparin. Thus, when the cannula is inserted into the catheter, it may remain in place, acting like a stopper, until a fluid sample is required. At that time, the assembly may be replaced with a similar assembly and a fluid sample thereafter taken. The needle assembly may then be removed from the catheter without disturbing the position of the catheter in the patient's vein.

Thus, one of the objects of the present invention is to provide an apparatus and method which utilize a prepositioned intravenous catheter and standard fluid collection containers to permit the collection of fluid samples from a single needle insertion site.

Another object of the present invention is to provide a fluid sampling apparatus and method which channel the fluid to be sampled along a single, short, straight route so that the opportunity for hemolysis, coagulation, or contamination is minimized.

A further object of the present invention is to provide a light, flexible adapter for fluid collection which can be inserted in a blood vessel without substantial patient discomfort and which avoids the necessity of establishing a second insertion site for fluid collection.

Yet another object of the present invention is to provide an alternative to the use of syringes as intermediate fluid collection devices so that the danger of vein deflation or collapse due to over-aspiration by syringe is reduced and the additional time and costs associated with use of syringes is minimized.

These and other objects and advantages of the present invention may be found in the drawings and disclosure which hereinafter follow.

DETAILED DESCRIPTION OF THE PREFERRED EMBODIMENTS OF THE INVENTION

Figure 1A:
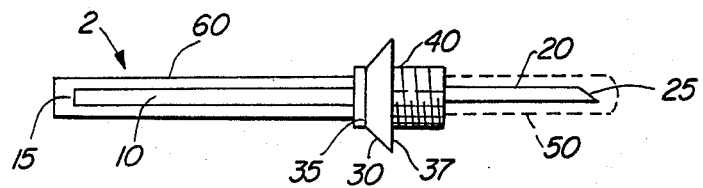
FIG. 1A is a side elevation view of the preferred embodiment of the present invention.

Referring to FIG. 1A, the needle assembly 2 of the present invention is shown. The needle assembly 2 comprises a cannula 10 made of a flexible material such as rubber, plastic, light weight metal or Teflon. The cannula 10 has a non-cutting edge 15. A rigid needle 20, which is made from light weight metal or synthetic material, is also provided. The needle 20 is provided with a tapered cutting edge 25.

Positioned between the cannula 10 and the needle 20 is a needle housing assembly 30. The housing assembly 30 has a first end 35 adapted to mate with a standard intravenous cannula and a second end 37, which is adapted to mount a flexible, rubber-like sheath 50 (shown by dashed lines) covering the needle 20. The second end 37 of the housing 30 is provided with threads 40 for purposes hereinafter disclosed.

In practice, it is preferred to maintain the sterility of the needle assembly 2. This is accomplished by providing a removable protective sheath 60, which covers the cannula 10, and by providing the flexible sheath 50, which covers the needle 20. It may be also advantageous to provide a removable protective sheath (not shown) covering the needle 20 and the flexible sheath 50. In addition to maintaining the sterility of the needle 20, the protective sheath 50 prevents fluid from escaping from the needle assembly until such time as sheath 50 is ruptured.

Figure 1B:
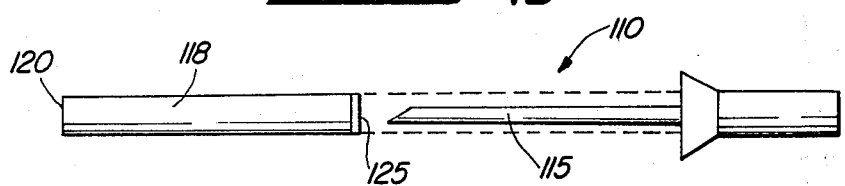
FIG. 1B is a side evaluation, exploded view of a standard needle-catheter assemply.

FIG. 1B shows the present invention in conjunction with standard medical devices. A needle assembly 110, which may be a standard assembly, such as that sold by The Deseret Company under the trademark Angiocath, is provided with a sharp, cutting needle 115. Surrounding the needle 115 is a catheter 118 (as shown in FIG. 1B, the catheter 118 is removed from the needle 115.) The needle assembly 110 is constructed such that after insertion of the needle 115 and the catheter 118 in the lumen of a vein, the needle 115 may be removed therefrom leaving a portion of the cathether 118 in the vein and a portion thereof exposed.

The cannula 10 of the needle assembly 2 is adapted for mating engagement with the catheter 118 so that the first end 15 of the cannula 10 does not extend beyond the first end 120 of the catheter 118. The first end 35 of the needle housing assembly 30 fits flush against the second end 125 of the catheter 118, providing an effective seal.

Figure 1C:
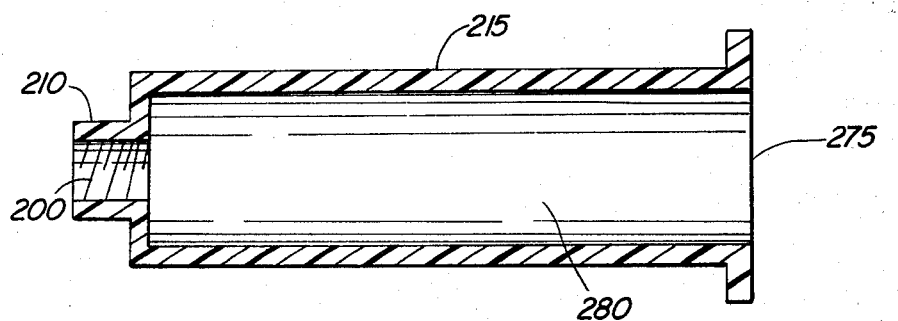
FIG. 1C is a side view of a standard collection holder.

In the preferred mode, the threads 40 on the second end 37 of the needle housing assembly 30 are matingly engaged to threads 200 which lie along in the tip 210 of a fluid collection container holder 215 (see FIG. 1C). The holder 215 may be a device similar to that sold by Monoject or Becton-Dickinson under the trademark Vacutainer.

Figure 1D:
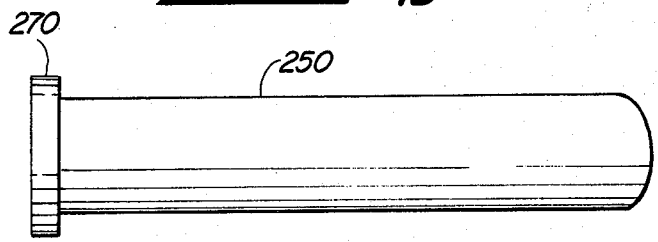
FIG. 1D is a side view of a standard collection container.

A fluid collection container 250 (see FIG. 1D) which has been evacuated to less than atmospheric pressure and which is maintained in that condition by a rubber stopper 270 is also used. The container 250, which is sized for insertion into the holder 215, is inserted into the second end 275 of the fluid collection container holder 215 and positioned within the bore 280 of the holder 215.

Figure 2:
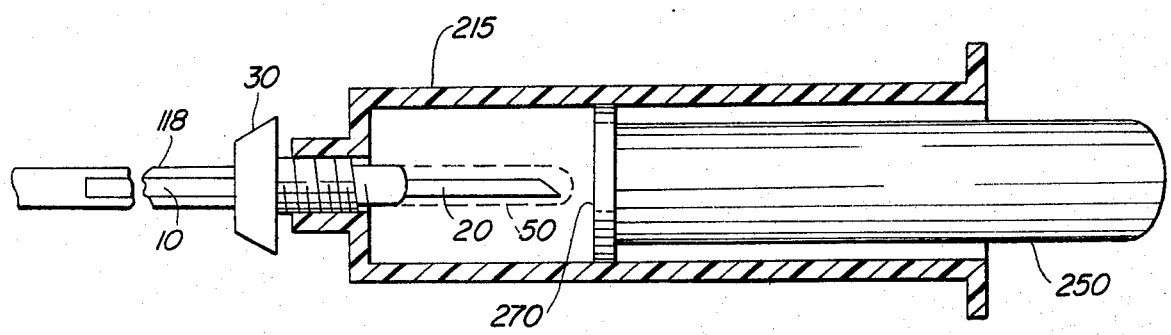
FIG. 2 is a cross-sectional view of the present invention showing the standard collection holder and collection container in place immediately prior to obtaining a fluid sample.

FIG. 2 depicts the configuration of the present invention as used in drawing fluid from a patient. The catheter 118 is first inserted into the patient's vein either to extract fluid or to introduce blood or fluid into the vein in a manner known in the art and the needle assembly 110 is removed thereform. The cannula 10 of the needle assembly 2 is inserted in the catheter 118 until the second end 125 of the catheter 118 makes an effective fit with the first end 35 of the needle housing assembly 30. In the preferred mode, the second end of the needle housing assembly 37 is threadably coupled to the fluid collection holder 215. The evacuated fluid collection container 250 is inserted into the bore 280 of the holder 215. The rubber stopper 270 of the first end of the fluid collection container 250 is pressed against the flexible sheath 50 and the cutting edge 25 of the needle 20. Additional pressure causes the cutting edge 25 to pierce the flexible sheath 50 and the rubber stopper 270, thereby causing blood to flow from the blood vessel (not shown) through the bores of the cannula 10 and the needle 20 in sequence and into the collection container 250. When the container 250 is removed, the sheath 50 returns to its original position around the needle 20, thus breaking fluid communication. The needle assembly 2 may thereafter be removed from the catheter 118 while leaving the catheter 118 in place in the patient's vein.

It should be apparent from the foregoing that various modifications, alterations, and changes may be made in the embodiment as illustrated and described herein without departing from the spirit and scope of the present invention as defined in the appended claims. In particular, while the invention has been described with reference to blood vessels, it will be appreaciated that other containers containing blood or other liquids may be sampled in the same way. Likewise, while the invention has been described in the preferred mode in conjunction with a standard collection container holder, an identical holder is not necessary and a blood collection container can be used without such a holder or with a modified holder.

What is claimed is:

1. A fluid sampling apparatus, which comprises:
   a. a flexible, non-cutting cannula;
   b. a rigid, cutting needle aligned longitudinally with said cannula;
   c. a needle housing assembly joining said cannula and said needle along the longitudinal axes thereof, said assembly having a first end adapted for sealing engagement with the exposed end of a catheter prepositioned in the lumen of a blood vessel, said assembly also having a threaded second end;
   d. each end of said needle housing assembly adapted for receipt of a segmented, removable protective cover encompassing said cannula and said needle; and
   e. a soft, flexible sheath connected to said second end of said needle housing assembly and covering said needle in spaced apart relation.

2. The apparatus of claim 1, wherein said cannula is adapted to fit slidably and frictionally within said prepositioned catheter, with said needle being provided with a cutting edge.

3. The apparatus as claimed in claim 1, wherein said cannula is coated with anticoagulation agent to prevent blood coagulation.

4. A method of obtaining fluid samples from a patient comprising the steps of:
   a. inserting a catheter into the lumen of a blood vessel of a patient;
   b. inserting a non-cutting, flexible cannula attached to a first end of a needle housing assembly into the bore of said catheter;
   c. removably engaging a fluid collection container to a needle at a second end of said needle housing assembly, said needle being provided with a cutting edge and being spaced apart from said cannula by said needle housing assembly.

5. The method of claim 4, wherein said removably engaging step further includes the step of matingly engaging a fluid collection container holder to the second end of said needle housing assembly.

* * * * *

UNITED STATES PATENT AND TRADEMARK OFFICE
CERTIFICATE OF CORRECTION

PATENT NO.   :   4,409,990
DATED        :   October 18, 1983
INVENTOR(S)  :   Gil N. Mileikowsky It is certified that error appears in the above—identified patent and that said Letters Patent is hereby corrected as shown below:

Column 1, line 15, insert "second" before "needle".

Column 1, line 53, "cannula and" should be deleted.

Column 1, line 53, "needles" should be --cannula and needle--.

Column 1, line 55, "th" should be --the--.

Column 4, line 10, "thereform" should be --therefrom--.

Column 4, line 38, "appreaciated" should be --appreciated--.

Signed and Sealed this

Thirteenth Day of March 1984

[SEAL]

Attest:

GERALD J. MOSSINGHOFF

Attesting Officer       Commissioner of Patents and Trademarks